United States Patent [19]

Kirkpatrick

[11] Patent Number: 5,602,278

[45] Date of Patent: Feb. 11, 1997

[54] N-OXIDES AND DERIVATIVES OF CHLORAMBUCIL FOR TREATING HYPOXIC TUMOR CELLS

[76] Inventor: Lynn Kirkpatrick, 29 Palmer Crescent, Emerald Park, Saskatchewan, Canada, S4L 1A2

[21] Appl. No.: 326,327

[22] Filed: Oct. 20, 1994

[51] Int. Cl.$^6$ .......................... C07C 229/28; C07F 9/547
[52] U.S. Cl. .............................................. 562/452; 564/13
[58] Field of Search ................................ 562/452; 564/13

[56] References Cited

FOREIGN PATENT DOCUMENTS 30-5073  7/1955  Japan .

OTHER PUBLICATIONS

International Conference on Bioreductive Drug Activation Aug. 16–19, 1994—Denny et al.
Mann, et al.—J. Chem. Soc. Perkin Trans. 1 (1991) pp. 2961–2964.
Owari, S.; Pharm. Bull. (Japan) 1:353–357 (1953), Transformation reaction of nitrogen mustard N–oxides in aqueous solution.
Aiko, S., et al.; Pharm. Soc. Japan 72:1297–1300 (1952), Nitrogen mustard N–Oxide and its effect on the Yoshia sarcoma.
Ishidate, M. et al.; Japan 5073 Jul. 28, 1953, Chemotherapeutic agents for agents for cancer.
Stahmann, M. S. et al.; J. Org. Chem. 11–586–591 (1946). Chemical Reactions of the Nitrogen Mustard Gases, VIII. The Oxidation of the Nitrogen Mustard Gases by Peracids, Mar. 1946.
Sakurai, Y. et al.; Pharm. Bull. (Japan), 1:297–301 (1953) N–Oxides of 2–Chloroethylamine Derivatives,.
Ishidate, M. et al.; Japanese Patent 6170 (1953).
Degutene, Y. et al.; J. Org. Chem. USSR7:1433–1435 (1971), p–[Di(2–chloroethyl)amino]Phenylakanoic acid N–oxides.

Degutis, Y. et al., J. Org. Chem. USSR6:1835–1837 (1970) N–substituted N–2–chloroethylaniline N–oxides. Describes synthesis of aromatic N–oxide derivatives. No biological activity was supplied.
Denny, W. A. et al.; Chlorambucil N–oxide: A Reappraisal of its Synthesis, Stability, and Selective Toxicity for Hypoxic Cells; International Conference on Bioreductive Drug Activation, Lake Tahoe, California, USA (1994).
Kirkpatrick, D. L. et al.; Synthesis and Bioreductive Potential of a Mono N–oxide Derivative of the Alkylating Agent Chlorambucil; Anti–Cancer Drugs 5:467–472 (1994).
Kirkpatrick, D. L. et al.; Selective Conditions for Bioreductive Activation of the Prodrug, Chlorambucil N–oxide; Proc. AACR 35:3778 (1994).
Mann, J. et al.; Synthesis of Novel N– and S–Mustards as Potential Pro–drugs Activated by Bioreductive Processes; J. Chem. Soc. Perkin Trans. 1:2961–2964 (1991).

Primary Examiner—Gary Geist
Assistant Examiner—Joseph M. Conrad, III
Attorney, Agent, or Firm—Morrison & Foerster LLP

[57] ABSTRACT

This invention relates to compounds which are N-oxides and derivatives of chlorambucil and which, under certain conditions, (1) are stable in hypoxic and oxic cells, (2) are toxic in cells having varying degrees of hypoxia, and (3) show little toxicity to oxic cells. These compounds have the general formula set out below and are used to treat tumorous cells:

$$R-N\begin{array}{l}OCH_2CH_2Cl\\ CH_2CH_2Cl\end{array}$$

wherein R is an alkyl, aryl, or derivatives thereof, such as $CH_3OCH_2CH_2-$;  $CH_3CH_2OCH_2CH_2-$; $C_6H_5OCH_2CH_2-$; $C_6H_5CH_2-$; $CH_3(CH_2)_3OCH_2CH_2Cl$; or any one of the following:

$$\text{—}\bigcirc\text{—}(CH_2)_3COOH$$

-continued
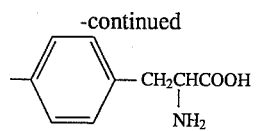
13 Claims, 12 Drawing Sheets wherein R is an alkyl, aryl or derivatives thereof, or any of the following:

N-OXIDES AND DERIVATIVES OF CHLORAMBUCIL FOR TREATING HYPOXIC TUMOR CELLS

FIELD OF THE INVENTION

The present invention relates to N-oxides and derivatives of chlorambucil for use in treating hypoxic tumor cells. In a hypoxic environment, the N-oxide derivatives of this invention convert to chlorambucil. In an oxic environment, the N-oxide derivatives are stable and non toxic, under certain conditions, and do not convert to chlorambucil. The present invention includes a method of treating hypoxic tumor cells by administering a pharmaceutical formulation containing N-oxide derivatives.

BACKGROUND OF THE INVENTION

Cancer control consists of three components: prevention, early detection, and treatment. Although prevention and early detection present the best opportunities to cure cancer, the majority of research focuses upon treatment.

Many cancers are treatable and some are even curable (Tannock et al., 1987). However, treatment can be toxic not only to tumor cells, but also to normal cells and tissue and may be resisted by tumorous cells. To overcome these problems, researchers have sought to exploit differences between normal and tumorous cells and tissue.

First Difference—One difference between normal and tumorous cells is the amount of oxygen in the cells. Many tumorous cells of rodents and humans are oxygen deficient and are "hypoxic" (Moulder et al, 1987; Vaupel et al, 1989) (in contrast to oxygenated cells which are "oxic"). These hypoxic cells limit the cure rate of standard radiotherapy (Disch et al., 1983; Gatenby et al., 1988) and possibly some anticancer drugs (Tannock et al; 1987; Sartorelli et al., 1988). It has been shown that hypoxic cells are resistant to radiotherapeutics and chemotherapeutics (Siemann, 1992; Hill, 1987; Bremner, 1990; Workman, 1992; Coleman, 1988; Workman, 1993).

Subpopulations of cells in solid tumors, such as those of the breast, colon, brain, head and neck, are hypoxic (Rockwell, 1983). In the 1970's, hypoxia in solid tumors was suspected and, in the 1980's, was confirmed (Siemann, 1992; Brown, 1979; Chaplin, 1987; Brown, 1979). Drug resistance in solid tumors may be caused by hypoxia (Rice et al., 1988). It has been shown that increasing the oxygen levels in experimental tumors decreases resistance to radiotherapy while decreasing the oxygen levels increases resistance to radiotherapy (Siemann, 1992; Bremner et al., 1990; Workman, 1993; Olive et al., 1992).

Hypoxic cells of solid tumors are resistant to chemotherapy for a number of reasons: lacking a normal cell growth cycle, they are insensitive to cycle-specific agents (Bremner et al., 1990); their location makes them poorly accessible to cytotoxic drugs; and their lack of oxygen affects the activity of drugs which have oxygen-dependent processes (Bremner et al., 1990).

Tumor cells become hypoxic as they multiply. Those cells close to a blood supply receive the necessary oxygen for proliferation. As the cells multiply and the tumor enlarges, the rapid cell growth exceeds the vascular development reducing the tumor's supply of oxygen (Vaupel et al; 1989; Siemann; 1992; Brown, 1979). Consumption of oxygen by the cells near the supply limits the amount of oxygen available to cells away from the supply (Vaupel et al., 1989). This results in varying degrees of hypoxia.

Tumor cells adjacent a blood supply are non-hypoxic, while those more than 120–150 mm away from a blood supply are chronically hypoxic (Vaupel et al., 1989). Between fully oxygenated cells and fully hypoxic cells are cells with varying degrees of hypoxia (Vaupel et al., 1989). Intermittent vascular occlusion or collapse results in acutely hypoxic cells.

Second Difference—Another difference between normal and tumorous tissue is related to this lack of oxygen. Reductive metabolic processes may be more prevalent in the hypoxic environment of solid tumors (Workman et al., 1993). Reductive enzymes reduce functional groups (such as N-oxides) having a potential to be reduced. Nitro compounds are reduced to amino derivatives and quinones are reduced to hydroquinones by enzymes such as DT-diaphorase, cytochrome $P_{450}$, cytochrome $P_{450}$ reductase and xanthine oxidase (Walton et al., 1989). It has recently been shown that DT-diaphorase levels tend to be elevated in human tumor samples from lung, liver, colon and breast cancers (Workman, 1994).

These two differences between normal and tumorous cells has led to the development of bioreductive antitumor drugs. These are drugs which exploit (1) the hypoxic nature, and (2) the reductive nature, of tumorous cells. These drugs are nontoxic and inactive until they are reduced by hypoxic cells thereby becoming toxic and active, cytotoxic agents (Workman, 1992).

A number of N-oxides have been examined recently for this bioreductive activity. One is the N-oxide derivative of 1,4-bis-{[2-(dimethyl-amino)ethyl]amino}. 5,8-dihyroxy-anthracene-9, 10-dione (AQ4N). This N-oxide is more toxic in vivo under conditions that promote transient hypoxia or which diminish the oxic tumor fraction (Patterson, 1993). Others are the mono-N-oxides of fused pyrazines, the lead compound of which is RB 90740. The N-oxide function is essential for the differential cytotoxic properties of these agents (Adams, 1992). Another is the aliphatic N-oxide of nitacrine, SN 24030. It has an exceptionally high selectivity for hypoxic cells (approximately 1500 fold) and an improved ability to diffuse into the extravascular compartment of tumors (Wilson et al., 1992). The N-oxide itself does not provide a reactive species but the reduction of this functional group unmasks an agent with cytotoxic potential However, so far, none of these N-oxides has been found to have clinical activity and to lack toxicity to normal cells and tissue.

One N-oxide derivative which has been studied with little success to date as an anti-tumor agent is the N-oxide derivative of chlorambucil (also known as a nitrogen mustard derivative). Chlorambucil is toxic to tumorous cells (McLean et al., 1979). Chlorambucil acts as an anti-tumor agent by cross-linking (or alkylating) DNA, preventing DNA from replicating and cells from growing. Chlorambucil has this effect in both tumorous and normal cells (Powis et al, 1991).

Previous studies on corresponding compounds have indicated potential for anticancer activity, but no selectivity under hypoxia. Japanese Patent No. 5073 (Ishidate and Sakurai), issued on Jul. 23, 1955, describes a method of manufacturing a related derivative of N-methyl nitrogen mustard N-oxide HCl (known as nitromin) namely, N-chloroethoxy N-chloroethyl N-methyl amine. The patent claims that this agent, the rearranged derivative of nitromin, is useful in treating cancer, but does not describe how to use the derivative to treat cancer, the relevance of hypoxia or whether this derivative converts to nitromin in vivo. Indeed, Ishidate later reported that nitromin was more stable but less reactive than N-methyl nitrogen mustard under the conditions tested (Ishidate et al. 1960). Ishidate showed that a lethal dose of nitromin which killed 50% of experimental animal was 50 times less toxic than its corresponding nitrogen mustard. Nitromin was found to be readily absorbed after oral administration and excreted rapidly, largely unchanged in the urine. This study, however, did not determine (1) the contribution of reductive enzymes to the in vivo cytotoxicity of nitromin, (2) whether nitromin is stable in hypoxic and oxic cells, (3) whether nitromin is toxic in cells having varying degrees of hypoxia, and non-toxic in oxic cells at corresponding concentrations.

A recent study of nitromin has shown that reduction by cyt $P_{450}$ reductase regenerates the potent bifunctional alkylating species N-methyl bis(B-chloroethyl)amine (White et al. 1992).

A number of persons have also recently studied the N-oxide derivative of chlorambucil to determine whether this agent would provide selective toxicity to hypoxic tumor cells. A study has reported that the N-oxide of chlorambucil is ineffective as an anti-tumor agent because this derivative is not preferentially toxic under hypoxia (Mann et al., 1991). A very recent paper again reported that the N-oxide of chlorambucil shows no enhancement of hypoxic selectivity beyond the value for chlorambucil (Denny et al. 1994).

Neither of these studies examined the effect of the N-oxide of chlorambucil under bioreductive conditions which might mimic conditions in vivo. The 1991 and 1994 studies (Mann et al. 1991; Denny et al. 1994) examined the N-oxide in vitro using cell lines which lack the levels of reductive enzymes which would be able to reduce the derivative. In addition, the 1960 study (Ishidate et al., 1960) examined nitromin in vivo using Ascities cells, which are oxygenated. Therefore all of these studies failed to mimic the hypoxic conditions of tumourous cells in vivo.

This inventor has reported that the N-oxide derivative of chlorambucil is less cytotoxic than chlorambucil and that under hypoxic conditions its cytotoxicity and metabolism are potentiated by the presence of reducing enzymes (Kirkpatrick et al., 1994; Kirkpatrick et al., 1994). These studies have been discounted by others who were unable to demonstrate the selective toxicity of chlorambucil N-oxide under hypoxic conditions (Denny et al., 1994).

Thus, apart from this inventor's work, published papers on N-oxide derivatives of chlorambucil have maintained that such derivatives show either weak or no enhancement of cytotoxicity under hypoxic conditions. Thus, there is a need to develop N-oxide derivatives of chlorambucil which (1) are stable in hypoxic and oxic cells, (2) are toxic in cells having varying degrees of hypoxia, and (3) show little toxicity to oxic cells.

In this application, "CaNT" tumor cells means CaNT murine adenocarcinoma cells. "CHL" means chlorambucil, which is a nitrogen mustard, and its variants. "CHL-HD" means 4-[p-(N-2-chloroethoxy N-2-chloroethylamine)phenyl] butanoic acid or the hydroxylamine form of chlorambucil. "CHLN-O" means an N-oxide derivative of chlorambucil. "EMT6" cells means mouse mammary tumour cells. "HYDRAL" means hydralazine. "Hypoxic" or "hypoxia" means oxygen deprived. "NBP" means 4-(p-nitrobenzyl)pyridine (NBP). "NADPH" means nicotinamide adenine dinucteotide phosphate in reduced form. "Oxic" means oxygenated. "SF" means survival fraction. "Tumor" or "tumorous" means cancerous cells or tissue.

BRIEF SUMMARY OF THE INVENTION

This invention relates to compounds which are N-oxides and derivatives of chlorambucil and which, under certain conditions, (1) are stable in hypoxic and oxic cells, (2) are toxic in cells having varying degrees of hypoxia, and (3) show little toxicity to oxic cells. These compounds have the general formula set out below and are used to treat tumorous cells:

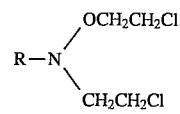

wherein R is an alkyl, aryl, or derivatives thereof, such as $CH_3OCH_2CH_2-$; $CH_3CH_2OCH_2CH_2-$; $C_6H_5OCH_2CH_2-$; $C_6H_5CH_2-$; $CH_3(CH_2)_3OCH_2CH_2Cl$; or any of the following:

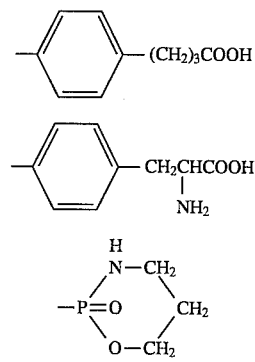

The invention also relates to 4-[p-(N-2-chloroethoxy N-2-chloroethylamino) phenyl] butanoic acid; a compound which (1) is stable in hypoxic and oxic cells, (2) is toxic in cells having varying degrees of hypoxia, and (3) shows little toxicity to oxic cells. This compound has the formula set out below and is used to treat tumorous cells:

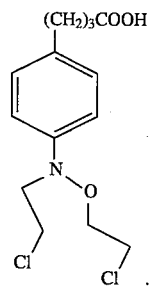

The invention also relates to the N-oxide of chlorambucil; a compound which is (1) is stable in hypoxic and oxic cells, (2) is toxic in cells having varying degrees of hypoxia, and (3) shows little toxicity to oxic cells. This compound has the formula set out below and is used to treat tumorous cells:

$$\text{(CH}_2\text{)}_3\text{COOH}$$

[structure: phenyl ring with (CH₂)₃COOH para to N⁺(O⁻)(CH₂CH₂Cl)(CH₂CH₂Cl)]

The invention also relates to salts of the above compounds. The salt would generally have the formulas set out below, wherein X is a salt, and may be HCl, tosylate or picrate, and wherein R is as set out above (page 7–8).

$$R-N\begin{array}{c}O\\ \uparrow\\ \\ \end{array}\begin{array}{l}OCH_2CH_2Cl\\ \\ CH_2CH_2Cl\end{array} \quad X$$

The invention also relates to pharmaceutical formulations containing such compounds. The formulation may also comprise one or more of such compounds together with one or more of (1) a pharmaceutically acceptable carrier, (2) a diluent, (3) an aqueous solution, (4) an adjuvant, or (5) another compound useful in treating hypoxic tumor cells.

The invention includes a method of medical treatment comprising the use of such compounds for hypoxic tumor cells. The method may also comprise using such compounds together with other methods of medical treatment useful in treating cancer, such as radiotherapy or chemotherapy.

DETAILED DESCRIPTION OF THE INVENTION

Figure 1:
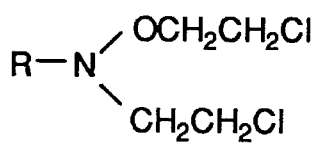
FIG. 1 shows the compounds of this invention.
Figure 1:
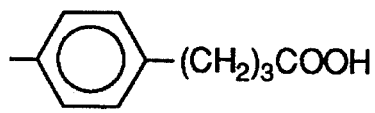
Figure 1:
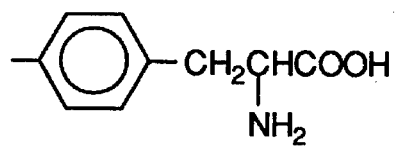
Figure 1:
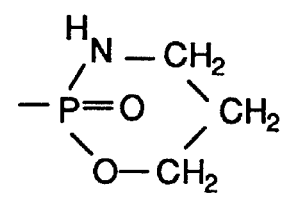

N-oxide hydroxylamine derivatives of chlorambucil are derivatives having the general formula shown in FIG. 1. According to this invention, these derivatives (1) hypoxic and oxic cells, (2) are toxic in cells having varying degrees of hypoxia, and (3) show little toxicity to oxic cells. These compounds or their salts (for example, HCl, picrate or tosylate) are useful in treating tumorous cells.

Figure 2:
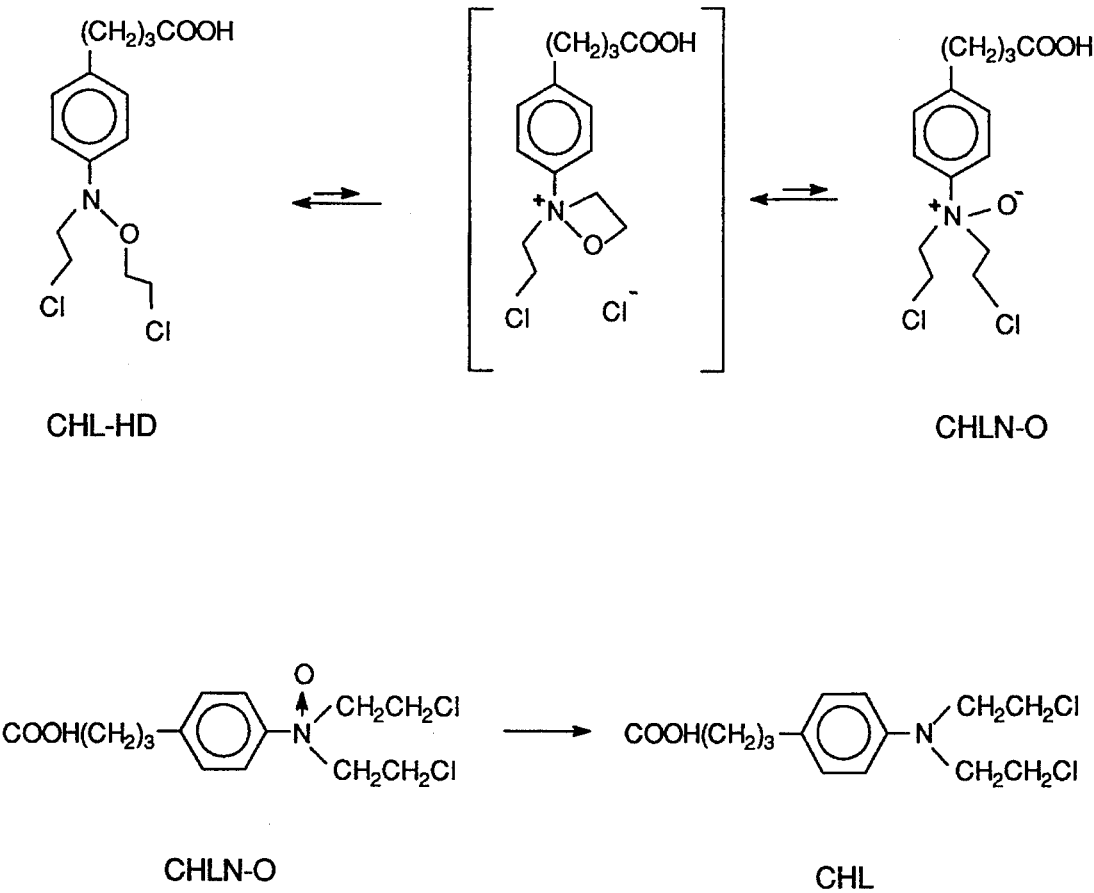
FIG. 2 shows the conversion of one of the compounds of this invention, CHL-HD to CHLN-O, and the conversion of CHLN-O to CHL.

Chlorambucil has the formula shown in FIG. 2 as CHL. The bis-chloroethyl amine group (the group with the nitrogen and two chloroethyl groups) of chlorambucil is reactive (Erlichman, 1987) and destabilizes chlorambucil. The nitrogen of the bis-chloroethyl amine has a lone pair of electons which is responsibility for the reactivity of chlorambucil.

Figure 11:
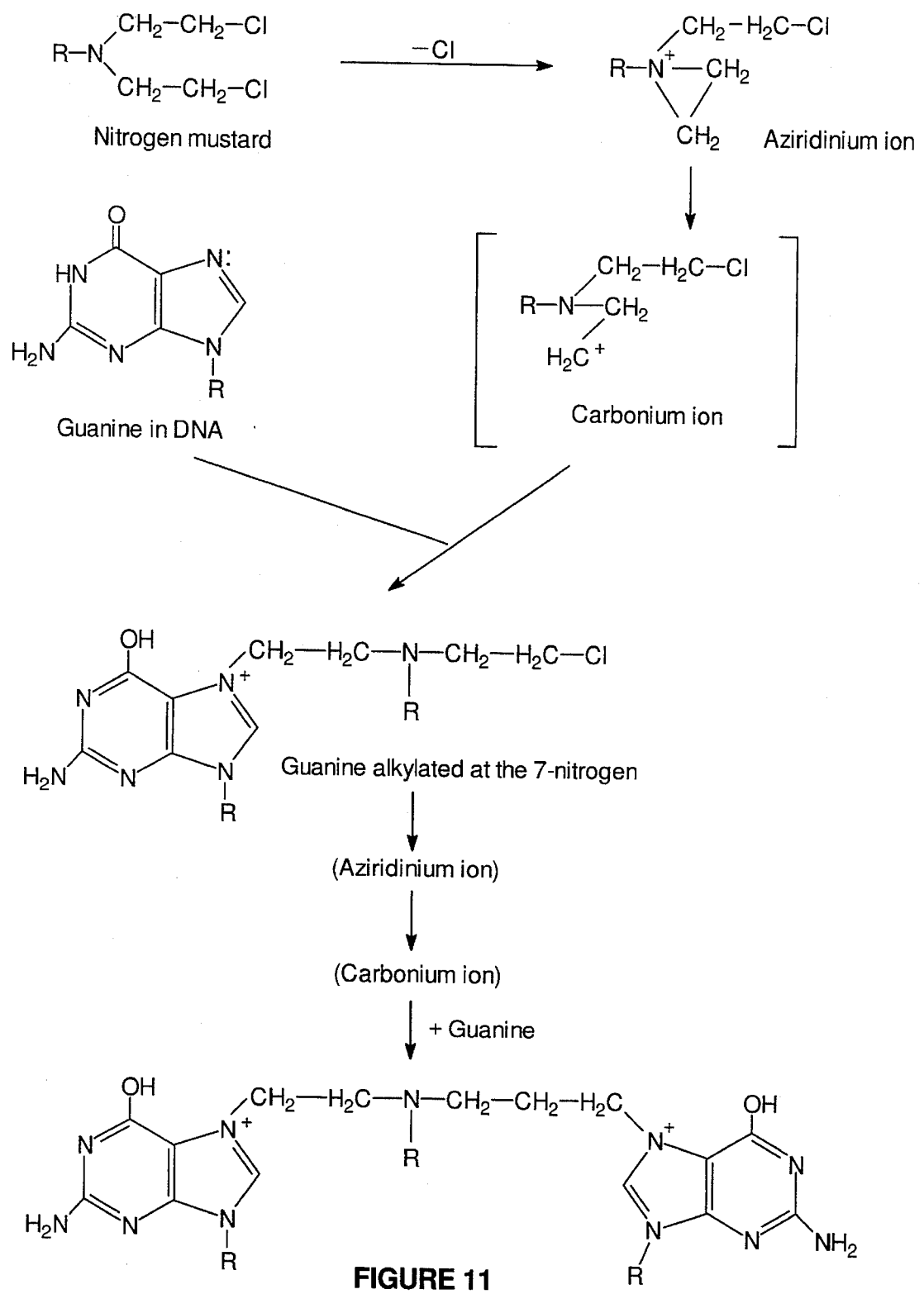
FIG. 11 shows how CHL crosslinks DNA. The structure of the nitrogen mustard with the R function represents CHL.
Figure 12:
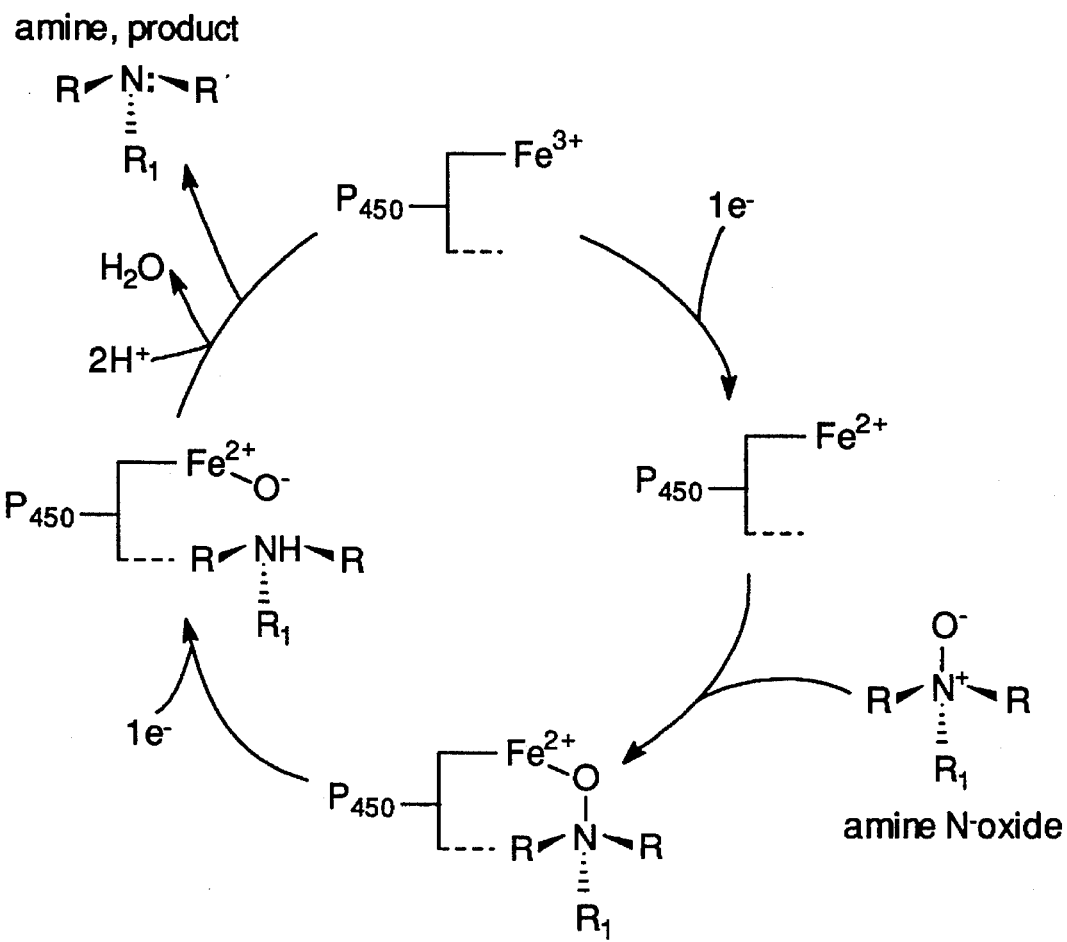
FIG. 12 shows how CHLN-O is reduced to CHL by the microsomal enzyme cyt $P_{450}$.

FIG. 11 shows how CHL crosslinks DNA. The structure of the nitrogen mustard with the R function represents CHL. By cross-linking DNA, CHL prevents cells from multiplying.

The invention also relates to 4-[p-(N-2-chloroethoxy N-2chloroethylamino)phenyl] butanoic acid ("CHL-HD"), a compound useful in treating tumorous cells. This compound is (1) stable in hypoxic and oxic cells, (2) toxic in cells having varying degrees of hypoxia, and (3) non-toxic in oxic cells. This compound has the formula shown in FIG. 2 as CHL-HD.

As an example, the hydroxyl amine of chlorambucil, CHL-HD was synthesized according to reported methods (Mann et al., 1991; Kirkpatrick, 1994) and as described below (see Example 2). Although reported as CHLN-O, it was the CHL-HD derivative of chloroambucil which was synthesized. As a further example, the N-oxide derivative of chrorambucil, CHLN-O , was synthesized as described below (see Example 3).

The N-oxide derivative of chlorambucil, CHLN-O, rearranges in aprotic solvents to the more stable hydroxylamine derivative, CHL-HD is shown in FIG. 2. This rearrangement has been described previously (Owari, 1953; Denny et al., 1994). However, CHL-HD also converts to CHLN-O. As CHLN-O is converted to CHL in a hypoxic environment (as shown in FIG. 2), more CHL-HD would convert back to CHLN-O.

Owing to the structural features of CHL-HD, one would not expect it to be selectively toxic under hypoxia. One would expect CHL-HD to act similarly to any nitrogen mustard, and one would expect it to be less potent than other mustard agents (Mann et al., 1991; Denny et al, 1994).

Although CHL-HD is structurally related to chlorambucil, its activity is much different. Trapping studies (to measure alkylating ability i.e. the potential ability of the agent to crosslink DNA) have shown that CHL-HD does not alkylate extensively unless reductively metabolized (see Example 6). Since this would not occur in most normal tissues in the body, CHL-HD would be less toxic than other alkylating agents in use as an anti-cancer drug. In vivo studies have shown that CHL-HD is 20 fold less toxic than CHL yet its ability to kill tumor cells is potentiated by hydralazine whereas that of CHL is not (see Example 7). Specifically, CHL-HD would be useful in targetting solid tumors which are traditionally very difficult to treat.

According to this invention, in vitro and in vivo results showed that the biological activities of the N-oxide derivative of chlorambucil (CHLN-O) and of the hydroxylamine derivative of chlorambucil (CHL-HD) are similar. Both compounds had a greater toxicity with reducing enzymes under hypoxia. Such biological activity was unexpected in view of the other reported results and in view of their molecular structure. Furthermore, both CHLN-O and CHL-HD are stable and produced minimal in vivo toxicity. This surprising in vitro and in vivo activity and minimal in vivo toxicity make compounds of the general formula shown in FIG. 1 promising to use in pharmaceutical formulations for treating hypoxic tumor cells. Suitable formulations may include buffered solutions containing one or more of the compounds administered as an intravenous infusion.

CHL-HD has shown enhanced activity as compared to radiation when administered concomitantly with hydralazine (to ensure tumor hypoxia) (Chaplin, 1989). This activity is enhance when the extracellular pH is lowered below the physiological 7.4. Since solid tumors are known to have subpopulations of hypoxic cells and commonly a pH in the range of 6.5 to 7.0 (Tannock et al., 1989), CHL-HD is expected to have solid tumor antineoplastic activity.

EXAMPLE 1

Materials

The supplies used in this patent application were obtained from the following sources: EMT6 cells-obtained from Dr. S. Rockwell, Yale University School of Medicine; bottles— glass milk dilution (Corning - from Baxter/Canlab, Mississauga ON); rat liver microsomes —isolated from livers of male Wistar rats (High Oaks Ranch, Baden, ON); male Wistar rats (High Oaks Ranch, Baden ON); NADPH (ICN Canada, Mississauga ON); NBP (Aldrich Chem Co. Milwaukee Wis.); rubber stoppers (Fisher Scientific, Nepean, ON); Gas mixtures — (Matheson Gas — Edmonton Alta); Chlorambucil (Sigma Chem. Co. St. Louis Mo. or ICN, St. Laurent, Quebec); peroxyacetic acid (Aldrich Chem Co. Milwaukee Wis.); Hamilton syringes (for injecting through rubber septa) (Fisher Scientific, Nepean, ON); tissue culture dishes (Falcon Labware, Baxter/Canlab, Mississauga ON); sucrose (Sigma Chem. Co. St. Louis Mo.); Waymouth's MB 752/1 medium (Gibco/BRL, Burlington ON); $NaHCO_3$ (Fisher, Scientific, Nepean ON); trypsin (Gibco/BRL, Burlington ON); Tris buffer pH 7.4 (ICN Canada, Mississauga ON or Sigma Chemical Co, St. Louis, Mo.). CO, $CO_2$, $N_2$ (Matheson Gas, Edmonton Alta); Clex (Dextran Products, Scarborough, ON.

EXAMPLE 2

Synthesis of CHL-HD

What was reported previously to be the synthesis of CHLN-O(Kirkpatrick et al., 1994) was actually the synthesis of CHL-HD (Denny et al., 1994).

A modified method of Mann et al., 1991, was used to synthesize CHL-HD. To a solution of CHN (ICN, St. Laurent, Quebec) 1 g, 6.6 mmol in dichloromethane (10ml) at 0° C. was added dropwise with stirring, 8 ml peroxyacetic acid (32% w/v in acetic acid). The mixture was stirred for 30 min. The resultant mixture was extracted three times with $H_2O$(50 ml), the organic layer dried over $CaCl_2$ and the solvent evaporated under reduced pressure at room temperature. The crude residue was chromatographed on a column of silica gel with petroleum ether (30°–60° C.) ethyl acetate (1:1) gradienting to 3:4 followed by petroleum ether:ethyl acetate:ethanol (95%) (3:4:0.5). The fractions containing the product were dried and flash chromatographed with petroleum ether:ethyl acetate (3:4) as an eluent. The N-oxide was produced as a light coloured low melting solid (m.p. 46.1° C.), $C_{14}H_{19}Cl_2NO_3$: calculated, C, 52.51%; H, 5.98%; N, 4.37%; found, C, 52.98%; H, 6.10%; N, 4.31%. $\delta H(200$ MHz; $CDCl_3$) 1.88 (2 H, m, $CH_2CH_2COOH$) 2.30 (2 H, t, $CH_2COOH$) 2.56 (2 H, t, $ARCH_2$) 3.41 (2 H, t, $NCH_2CL$) 3.65 (4 H, m, $NOCRCH_2Cl$, $NCH_2CH_2Cl$) 3.92 (2H,t, $OCH_2CH_2Cl$) 7.04 (4H,2×d $C_6H_4$) 11.80 (1 H, brs COOH).

Once isolated and dried, CHL-HD was found to be stable when stored at 0° C. or when in alcoholic solution.

EXAMPLE 3

Synthesis of CHLN-O

To a solution of CHL (ICN, St. Laurent, Quebec), 1g, 6.6 mmol in dicloromethane (10 ml) (Fisher) at 0° C. was added dropwise with stirring, 8 ml peroxy acetic acid (32% w/v in acetic acid)(Aldrich). The mixture was stirred for 60 min. The solvent of the resultant mixture was evaporated under reduced pressure at room temperature. The remaining residue was dissolved in 0.5ml acetone (Fisher) and 100 μl of concentrated HCl (Fisher) was added added at 0° C. Diethyl ether (Baker) was added to precipitate the product. The ether was decanted and the residue washed with deionized water. The residue was dried at room temperature in a desicator under vacuum over night. The resultant product was a hygroscopic solid, H (200MHZ; Acetone-D6) 1.94 (2 H, m, $CH_2CH_2COOH$) 2.35 (2H, t, $CH_2COOH$) 2.72 (2H, t, $ARCH_2$) 3.60 (2H, m, $NCH_2CH_2Cl$) 3.85 (2 H, m, $NCH_2CH_2Cl$) 4.50 (4H, m, $NCH_2CH_2Cl$) 7.60 (4 H 2 ×d $C_6H_4$)

EXAMPLE 4

Isolation of Rat Liver Microsomes

Male Wistar rats were provided food and water ad libitum and maintained under the standards of the Canadian Council on Animal Care. Rat liver fractions were prepared (Yasukochu et al., 1976). Following killing by gassing with $CO_2$, the liver was removed, washed in 0.25 M sucrose, weighed and minced on ice. The tissue was homogenized by 3 ×30 sec high speed bursts on a PRO 200 Homogenizer, DiaMed Lab Supplies Inc. Mississauga ON), and centrifuged (Sorvall RC-5B, Dupont Instruments, Newtown Conn.) 10,000 ×g for 15 min at 4° C. The supernatant was collected and centrifuged (L5-50 ultracentrifuge, Beckman Instruments, Canada, Mississauga ON) at 105,000 ×g for 65 min at 4° C. The microsomal pellet was assayed for protein content and cyt $P_{450}$ content. Cyt $P_{450}$ content was determined spectrophometrically, using a Hewlett-Packard 8452A Diode Array spectrophotometer (Mississauga ON) by monitoring its reduced CO difference spectrum at 400–500 nm (Masters et al., 1967).

EXAMPLE 5

In Vitro Cytotoxicity

Altering pH—To test in vitro cytotoxicity at pH 7.4 or 6.8, the pH of the medium was adjusted prior to gassing. Waymouth's MB 752/1 medium was dissolved in glassed distilled deionized water with 2.24g $NaHCO_3$ per liter and sterilized by filtration (Sterivex-Millipore Corp. Mississauga ON) to produce media of pH 7.4. Medium of lower pH (pH 6.8) was made using 0.56 g $NaHCO_3$ per liter.

Methodology—EMT6 mouse mammary carcinoma cells grown in monolayer were used to examine the cytotoxicity of CHL-HD under aerobic and hypoxic conditions. $1 \times 10_5$ cells in 10 ml Waymouth's MB 752/1 medium (pH 7.4) supplemented with 15% Clex (a semisynthetic serum substitute; Dextran Products, Scarborough, ON) were seeded into glass milk dilution bottles 3 days prior to drug exposure. On the day of experimentation, the medium in the bottles was exchanged with 10 ml fresh containing externally added reducing enzymes (rat liver microsomes isolated as previously described and a nicotinamide cofactor, (NADPH 1.3 mM). The bottles were fitted with rubber stoppers and gassed by inserting sterile needles (Yale-Baxter/Canlab, Mississauga ON) through the septum for 1.5 h with humidified 95% $N_2$/5% $CO_2$ to simulate the hypoxic environment of solid tumors. Parallel bottles were gassed with 95% air/5% $CO_2$ for aerobic conditions. CHL-HD was dissolved in ethanol just prior to cytotoxicity testing.

Following the pregassing period, 100 μl Of vehicle or drug was injected through the rubber septa of hypoxic and aerobic bottles without breaking the gas flow. The cells were treated for 6 h, following which gas was stopped, the medium was removed, the cells were washed with phosphate buffered saline and the cells were incubated with 5 ml 0.05% trypsin (37° C.) for 10 min. Medium (5 ml) was added to deactivate the trypsin and a 1 ml aliquot was taken to count the cells on a Coulter Counter (Coulter Electronics INC. Hialech FL). Dilutions of cells were plated into 5 ml medium in 60 mm tissue culture dished (Falcon, Baxter/Canlab, Mississauga ON) and placed into a $CO_2$ incubator (NAPCO model 5100, Portland Oreg.) for 10 days. Following the incubation the medium was washed off the cells and the cells were stained by exposing the crystal violet (2.5 g/L in methanol). The colonies containing more than 50 cells were counted and a plating efficiency was calculated as described below. The Percent Survival was determined by comparing the plating efficiency of the drug treated to the vehicle treated cells.

$$\text{PLATING EFFICIENCY} = \frac{\text{Number of colonies}}{\text{Number of cells plated}}$$

$$\text{PERCENT SURVIVAL} = \frac{\text{Plating efficiency (treated)}}{\text{Plating efficiency (vehicle)}} \times 100$$

Since solid tumors are known to have lower than physiological extracellular pH 7.4 (Tannock et al., 1989), it was felt that the cytotoxicity of CHL-HD should be examined at lowered pH values (6.8). The effect of pH on the activity of CHL-HD was determined by adjusting the pH of the medium to 6.8 prior to gassing and drug exposure. The cytotoxicity of CHL-HD was measured as described above.

Figure 3:
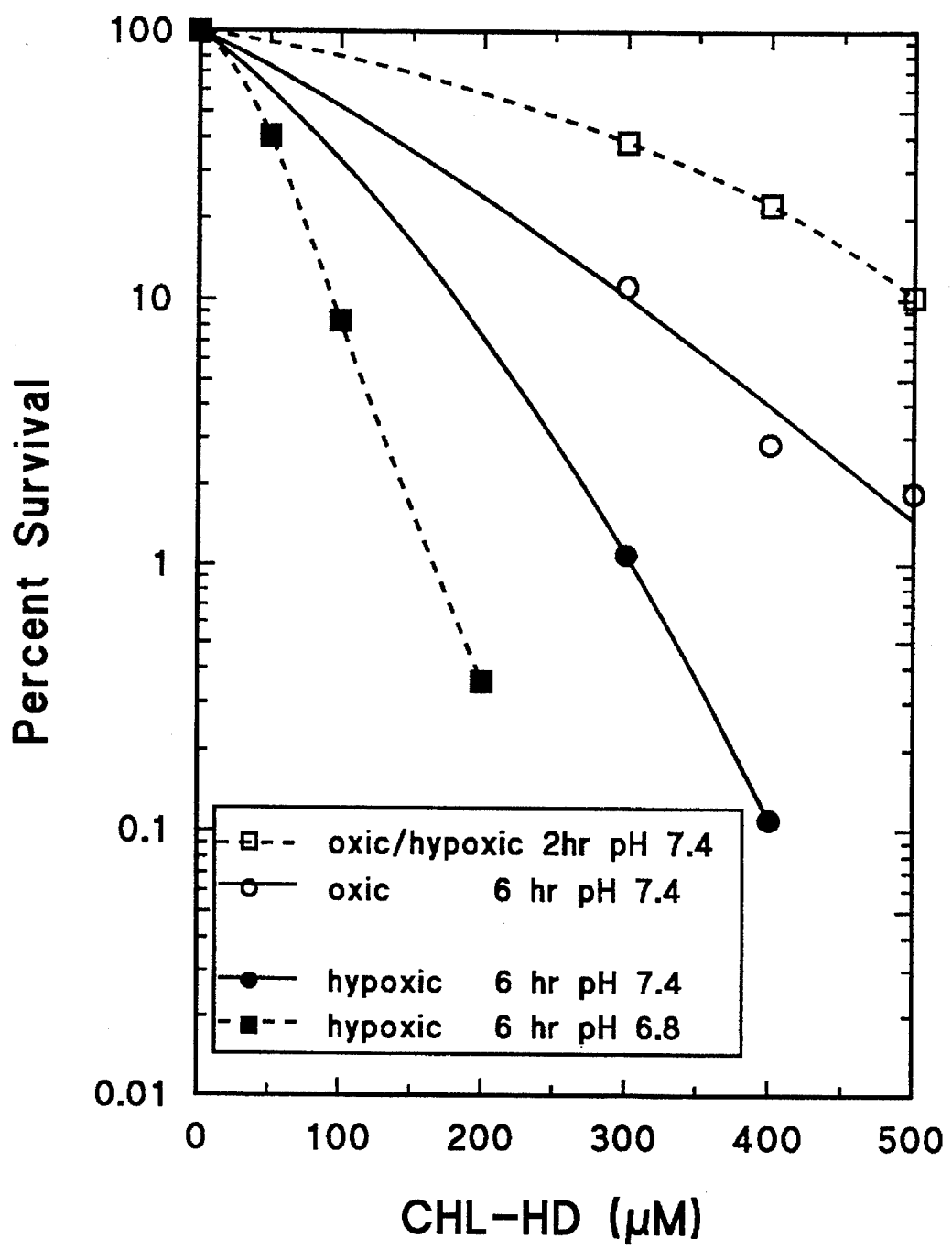
FIG. 3 shows the results of EMT6 cells in culture exposed to one of the compounds of this invention (CHL-HD) in the presence of microsomes under oxic or hypoxic conditions for 2 or 6 hours.

FIG. 3 shows the results of EMT6 cells in culture exposed to one of the compounds of this invention (CHL-HD) in the presence of microsomes under oxic or hypoxic conditions for 2 or 6 hours. The data demonstrates that both hypoxia and lowered pH in the presence of reducing enzymes potentiate to cytotoxicity of CHL-HD.

EXAMPLE 6

In vitro Metabolism and Alkylation

Using rat liver microsomes, nicotinamide cofactors and inhibitors, it was detemined that reducing enzymes, cofactors and hypoxia were needed to activate CHL-HD to an alkylating species.

Methodology—Glass milk dilution bottles containing 12ml microsomes in 0.1 M Tris, pH 7.4 were fitted with rubber septa and gassed with 95% $N_2$/5% $CO_2$ (0.5 mM) for 30 min at 37° C. Drug or vehicle (methanol) 50 μl, with or without NADPH (100 μl) were injected through a rubber septum into the medium allowing for uninterrupted gassing. Parallel studies were carried out under oxic conditions where reaction mixtures were placed in an atmosphere of 95% air/5% $CO_2$. Control incubations were conducted in the absence of nicotinimide cofactor, enzyme, drug or in the presence of boiled microsome preparation. Inhibition of the metabolism was studied by concomitant gassing with CO.

Aliquots of the reaction mixture (1 ml) were removed at consecutive time points after 0 to 8 h incubation. The aliquot was added to 2 volumes methyl ethyl ketone (MEK) (Fisher Scientific, Nepean, ON). The mixture was vortex-mixed (Fisher Scientific, Nepean, ON) 60 sec and centrifuged (1000 g for 5 min) (Megafuge, Baxter/Canlab, Mississauga ON). The organic layer was removed and placed in an evaporation tube (Sybron SC248 Sample Concentrator, Brinkman Instruments (Canada) LTD. Mississauga ON). The aqueous layer was again extracted with 1 ml MEK. The organic layers were combined and evaporated to dryness under vaccum at 20° C. (Sybron SC248 Sample Concentrator, Brinkman Instruments (Canada) LTD. Mississauga ON). The residues were stored at–20° C. (Fisher Scientific, Nepean, ON) until analyzed by HPLC chromatography as described previously (Chandler et al., 1993).

The determination of the ability of the reduced metabolite to alkylate 4-(p-nitrobenzyl)pyridine (NBP) was monitored. When alkylated the resultant species is blue.

Protein Determination—The microsomal fraction was diluted and assayed for protein content (Lowry et al., 1951 ) with bovine serum albumin as a standard.

NADPH Cytochrome $P_{450}$ Reductase —Cytochrome $P_{450}$ reductase activity was measured spectrophometrically by monitoring the reduction of cytochrome c at 550 nm using the procedure of Masters et al., 1967. The activity was calculated and reported as the reduction of μmol cytochrome c/min/mg protein.

Figure 6:
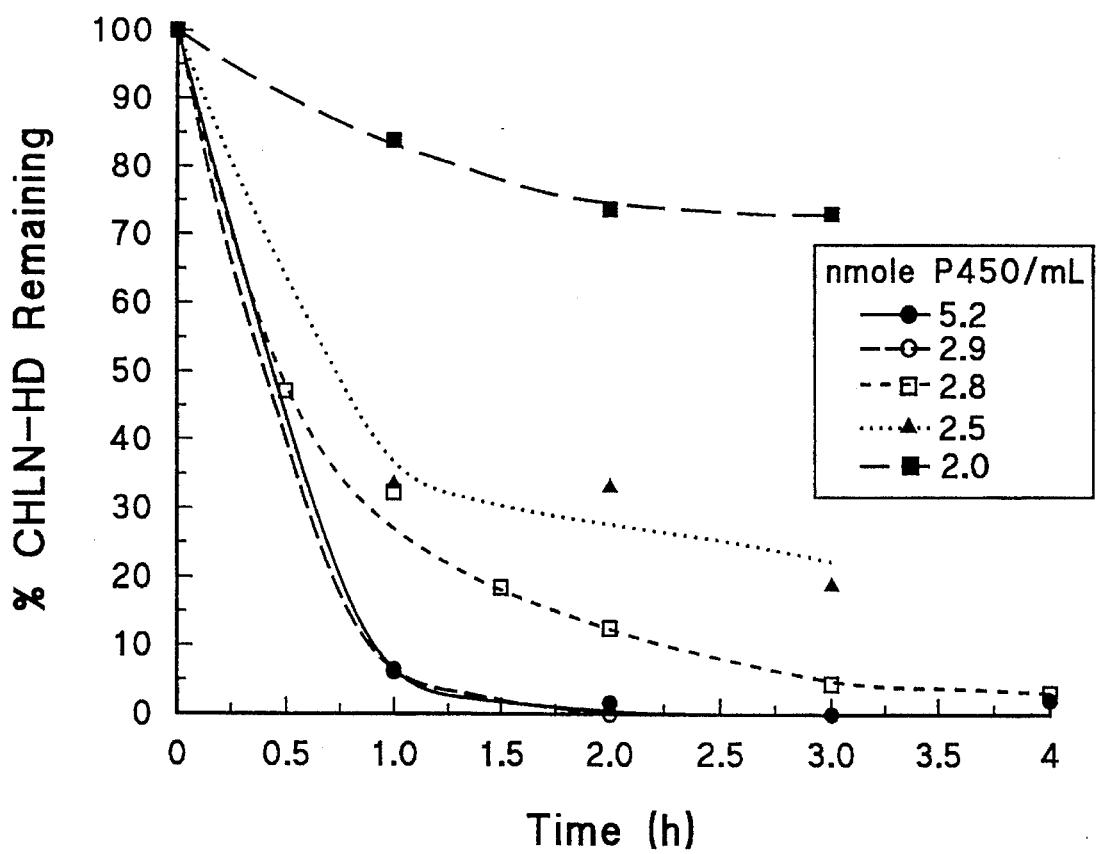
FIG. 6 shows the metabolism of CHL-HD in a hypoxic environment in the presence of NADPH (1 mM) and microsomes at 2.0–5.2 nmol cyt $P_{450}$/ml.

FIG. 6 shows the metabolism of CHL-HD by rat liver microsomes in vitro under various exposure conditions.

Figure 7:
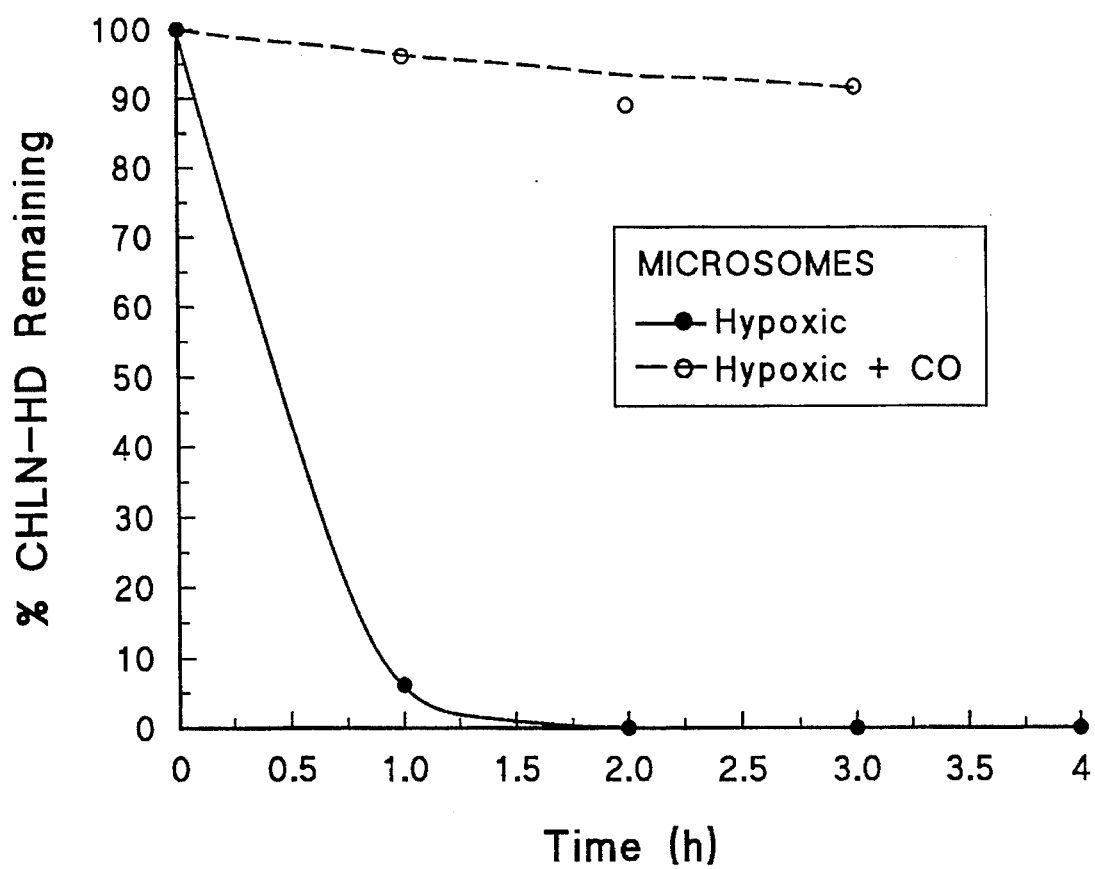
FIG. 7 shows the effect of CO on reductive metabolism of CHL-HD by rat liver microsomes (2.9 nmol cyt $P_{450}$/ml) and NADPH (1 mM) under hypoxia.

FIG. 7 shows the metabolism of CHL-HD in a hypoxic environment in the presence of NADPH (1 mM) and microsomes at 2.0–5.2 nmol cyt $P_{450}$/ml.

Figure 8:
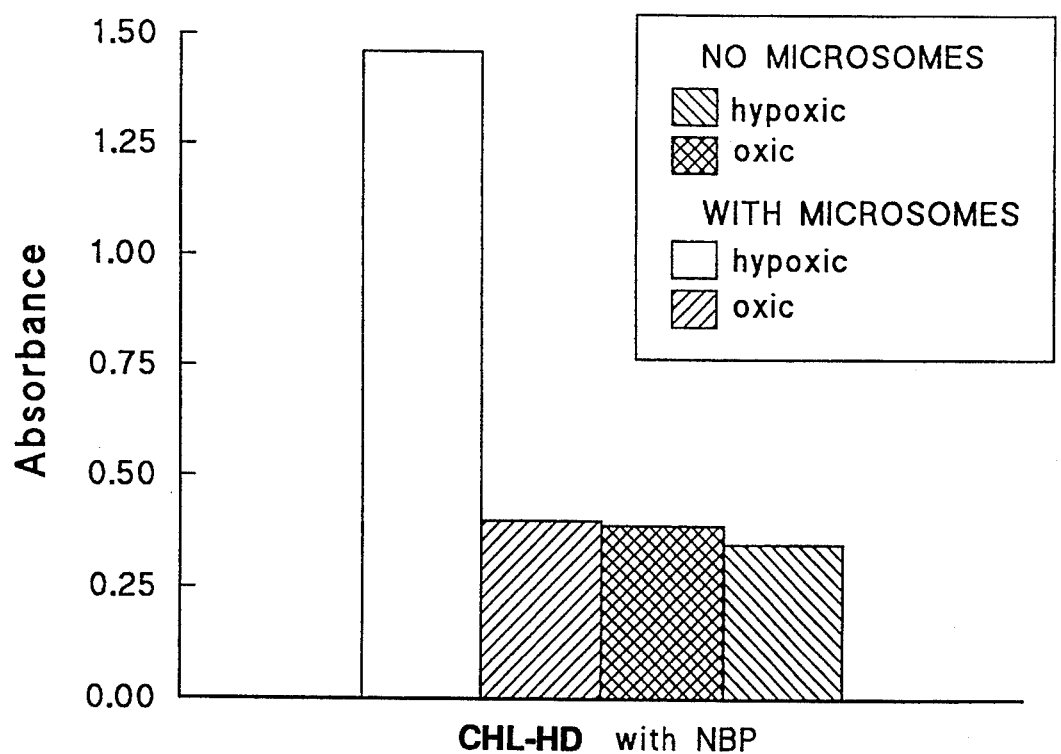
FIG. 8 shows the ability of one of the compounds of this invention (CHL-HD) to alkylate NBP after 18 hours incubation under oxic and hypoxic conditions in the presence and absence of microsomes (3nmol cytochrome $P_{450}$/ ml) and NADPH (0.5 mM).

FIG. 8 shows the effect of CO on reductive metabolism of CHL-HD by rat liver microsomes (2.9 nmol cyt $P_{450}$/ml) and NADPH (1 mN) under hypoxia.

Alylation by CHL-HD—To determine whether the reduction of CHL-HD would produce an alkylating species, the ability of CHL-HD and its reduced metabolite(s) to alkylate was tested using 4-(p-nitrobenzyl)pyridine (NBP) as a trapping agent. Incubation mixtures contained 2% v/v NBP (10% in acetone), microsomal enzymes in 0.1 M Tris buffer (pH 7.4; 12 ml total volume) and were gassed with $N_2$ 95%/$CO_2$ 5% for 30 min. The drug was injected with NADPH (0.5mM) through a rubber septum into the medium allowing for uninterrupted gassing. Control studies were carried out with chlorambucil (CHL) or vehicle, with or without microsomes, and under oxic conditions. Aliquots of the reaction mixture (1 ml) were removed at consecutive time points after 0 to 18 h incubations. Each reaction was terminated by the addition of 2 volumes acetone, 1 volume 1 M NaOH, and the sample extracted immediately with 4 volumes ethyl acetate. The organic and aqueous phases were separated by centrifugation for 2 min at 1000 g, and the absorbance of the organic layer at 540 nm was determined. The incubations and subsequent extractions were carried out under subdued light.

After 18 h incubation of CHL-HD (3 mM) under hypoxia in the presence of microsomes and reducing equivalents, the NBP-trapped species had an absorbance of 1.461 at 540 nm. FIG. 8 shows the ability of one of the compounds of this invention (CHL-HD) to alkylate NBP after 18 hours incubation under oxic and hypoxic conditions in the presence and absence of microsomes (3 nmol cytochrome $P_{450}$/ml) and NADPH (0.5 mM) (FIG. 8). CHL-HD (3 mM) in air, in the presence of microsomes and reducing equivalents, was able to form an NBP-bound species, although the absorbance (0.389) was less than one-third that of CHL-HD (3 mM) under the identical hypoxic conditions. Similar absorbances of 0.400 and 0.348 were observed under oxic and hypoxic conditions respectively, when microsomes and reducing equivalents were eliminated from the reaction mixture.

Figure 9:
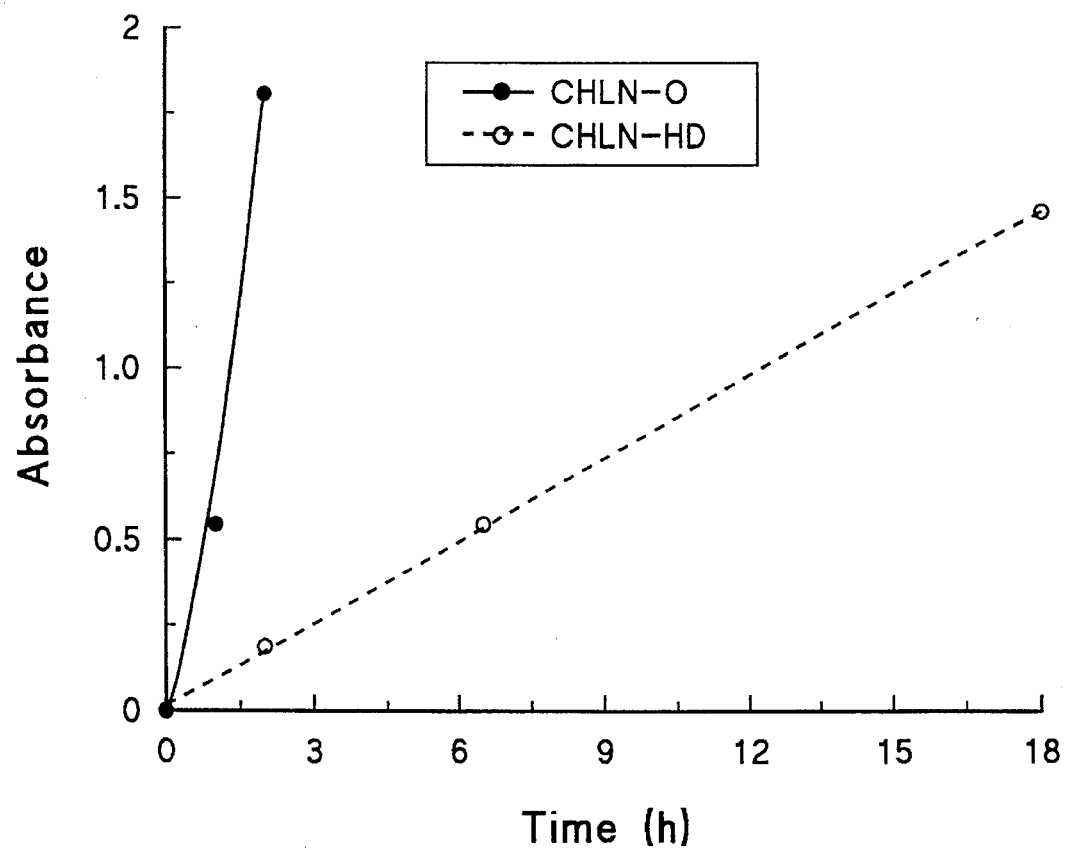
FIG. 9 shows the rate of formation of alkylated species with NBP by CHLN-O and CHL-HD.

Alykation by CHLN-O—CHLN-O(3 mM) was also evaluated for alkylating capacity, with or without microsomes, under hypoxia or oxia. In air, or in the absence of microsomes, CHLN-O reacted in the same manner as CHL-HD under the same conditions (FIG. 8), producing only low levels of alkylation. Under hypoxia in the presence of microsomes, the rate at which CHLN-O, formed an alkylating species was much faster than CHL-HD. FIG. 9 shows the rate of formation of alkylated species with NBP by CHLN-O and CHL-HD under hypoxia. Under hypoxia, in the presence of microsomes and reducing equivalents, an absorbance of 0.544 was observed after 1 h incubation and an absorbance of 1.81 was observed after 2 h with CHLN-O as compared to 1.461 after 18 h with CHL-HD. These data suggest that CHL-HD requires longer to produce an alkylating species, possibly due to the fact it must first rearrange to the CHLN-O before it can be activated by reduction.

Figure 10:
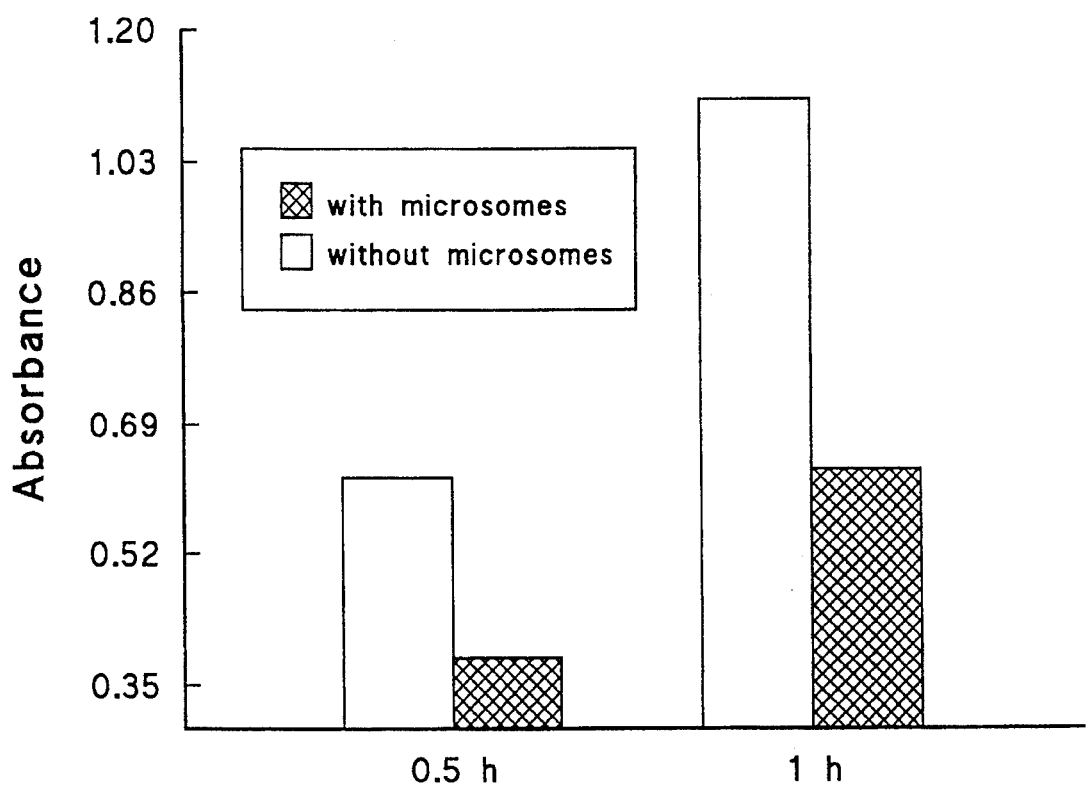
FIG. 10 shows the inhibitory effect of microsomes (3 nmol/ml cytochrome $P_{450}$) on the ability of NBP to trap CHL.

Alylation by CHL—The ability of the possible reductive metabolite, chlorambucil, to form a coloured product with NBP was investigated for comparison to the absorbances observed with CHL-HD. FIG. 10 shows the inhibitory effect of microsomes (3 nmol/ml cytochrome $P_{450}$) on the ability of NBP to trap CHL. In air, in the presence of microsomes and NBP, CHL (1.7 mM) produced an absorbance of 0.386 after 30 min and 0.630 after 1 h. The absorbance almost doubled when microsomes were eliminated from the mixture, resulting in absorbances of 0.619 after 30 min and 1.11 after 1 h. These data show that chlorambucil is so reactive that it alkylates the NBP and microsomes when both are present in the reaction mixture.

Figure 5:
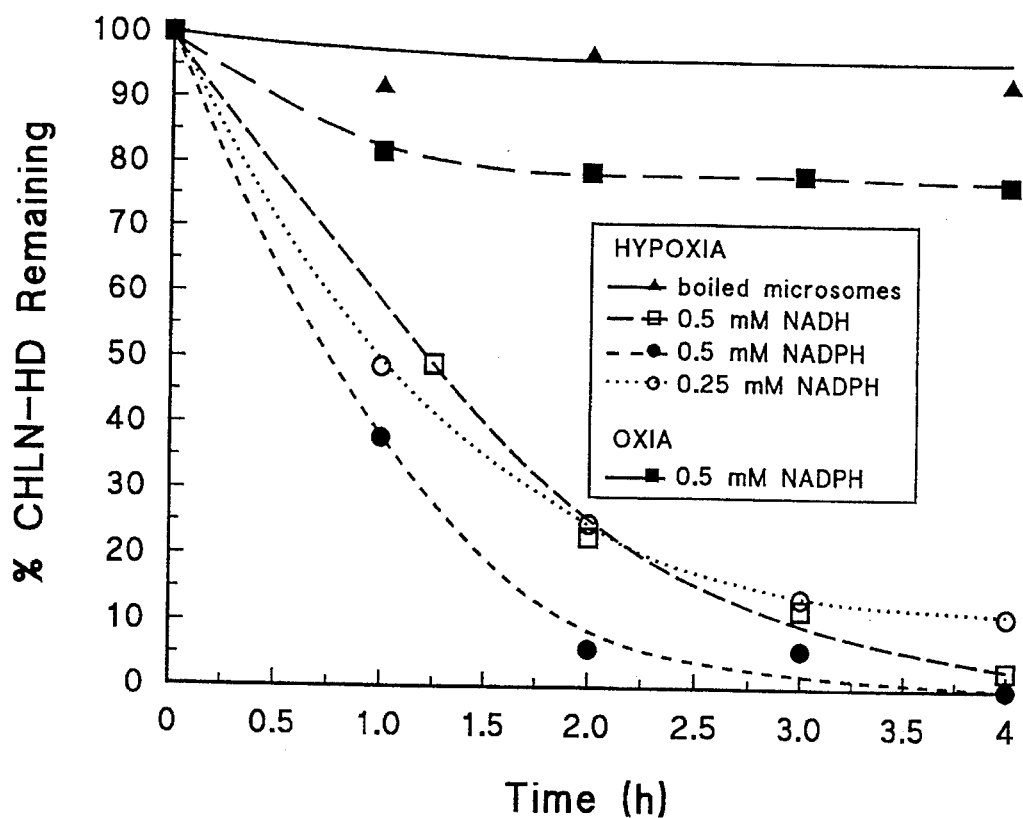
FIG. 5 shows the metabolism of CHL-HD by rat liver microsomes in vitro under various exposure conditions.

FIG. 5 illustrates that in air or in the presence of boiled microsomes (inactive enzymes with no reductive potential) very little if any metabolism of CHL-HD occurs. In the presence of microsomes and cofactors NADH or NADPH, under hypoxia, CHL-HD is metabolized. Additionally, in the presence of NADPH, metabolism occurs more readily at lower concentrations of cofactor suggesting a preferential role for cyt $P_{450}$ or cyt $P_{450}$ reductase in the metabolism of the agent.

FIG. 6 illustrates that there is a relationship between the amount of cyt $P_{450}$ in the metabolic reaction mixture and the rate of metabolism of CHL-HD.

FIG. 7 illustrates that CO inhibits the ability of microsomes to metabolize CHL-HD again indicating a role for cyt $P_{450}$ in this metabolism (as compared to some of the other enzymes present which wouldn't be affected by CO).

Summary —In summary, FIGS. 5–12 illustrate that CHL-HD requires hypoxia and reducing enzymes and cofactors to convert to an activated alkylating species which will be trapped by 4-nitrobenzylpyridine to form a colored complex. The bioreductive activation is compared to that of CHLN-O and CHL to substantiate that activation is occurring, but requires reduction and longer exposure time. The major enzyme responsible for the activation of CHL-HD appears to be cyt $P_{450}$.

EXAMPLE 6

In vivo cytotoxicity

CHL-HD has shown enhanced activity as compared to radiation when administered concomitantly with hydralazine (to ensure tumor hypoxia) (Chaplin, 1989).

The therapeutic potential of CHL-HD has been evaluated using an in vivo and in vitro assay against the CaNT murine adenocarcinoma. The moderately differentiated CaNT murine adenocarcinoma arose spontaneously in the Gray Laboratory mouse colony (Mount Vernon Hospital, Northwood UK). The tumors were implanted subcutaneously by injection of $10^5$ cells over the sacral region of the back of CBA/Gy fTO mice. Tumors were used when they achieved a mean diameter of 6–8 mm (approximately 14 days post implant).

CHL-HD was dissolved in Tris buffer pH 7.4. CHL (Sigma Chemical Co. St. Louis, Mo.), and hydralazine (Sigma Chemical Co. St. Louis, Mo.)), was dissolved in sodium carbonate 1% (Sigma Chemical Co. St Louis, Mo.)), and at 0.5 mg/ml water. CHL-HD (200 mg/kg) was injected intraperitoneally (i.p.) 5 minutes before or 30 minutes after, hydralazine (5 mg/kg). Three mice were used per treatment group and the studies were carried out on two separate occasions.

15 Gy radiation was delivered to mice placed in a lead tube which restrained them without anaesthetic and allowed the whole body to be shielded from the radiation beam except the superficial tumor which projected into the radiation beam. Radiation was supplied from a 240kV X-ray set (Pantak, Windsor UK) operating at 15mA (hvl =2.5 mm Cu). Mice breathed air during irradiation. Overnight, mice were fed food and water ad libitum.

After 18h, mice were killed and tumors excised aseptically. Tumors were weighed, minced and enzyme digested (using protease 1mg/ml, DNase I 0.5 mg/ml and 0.5 mg/ml collagenase (Sigma Chemical Co. St. Louis, MO.) with stirring at 37° C. for 1 h. After pipetting to break up remaining pieces, the supernatant was collected, enzymes neutralised with full culture media (see below) and centrifuged to pellet the cells. After resuspension in appropriate volume an aliquot was tested for trypan blue (Sigma Chemical Co. St. Louis, Mo.) exclusion for viability. Dilutions were then made in media and aliquoted in 8 ml into 9 mm dishes (Sterilin, UK). Each dish was also allocated 8 ml of heavily irradiated feeder cells (V79 fibroblasts) which condition the culture media, but do not form colonies during the period of growth of the surviving clonogenic tumor cells. Tumors cells were grown in Eagles Modified Minimal Essential Medium supplemented with 10% fetal calf serum (Gibco/BRL), sodium carbonate (Sigma Chemical Co. St. Louis, Mo.), glutamine, and penicillin and streptomycin (GIBCO/BRL). Cells were incubated in a Queue $CO_2$ incubator (Queue UK) at 37° C. humidifed with 5% $CO_2$. After 10 days media was discarded and colonies of tumor cells stained. Colony forming efficiency (CFE) was calculated from number of colonies divided by number of trypan blue excluding cells seeded per dish. Tumor surviving fraction was calculated from the product of CFE and cell yield (the relative number of cells released per 100 mg from the control and treated tumor); Control is plotted as unity and treated (normally less than unity) on a log scale for convenience.

CHLN-O was dissolved in a small amount of absolute ethanol (Merck, UK) then in Tris buffer (0.1 M titrated to pH 6.0 with HCl) so that final concentration of ethanol was not more than 1:30 v/v. In combination with hydralazine, CHLN-O was injected intraperitoneally 30 min after hydralazine.

Survival of the cells was determined using a previously described in vitro clonogenic assay (Parkins et al., 1993).

Figure 4A:
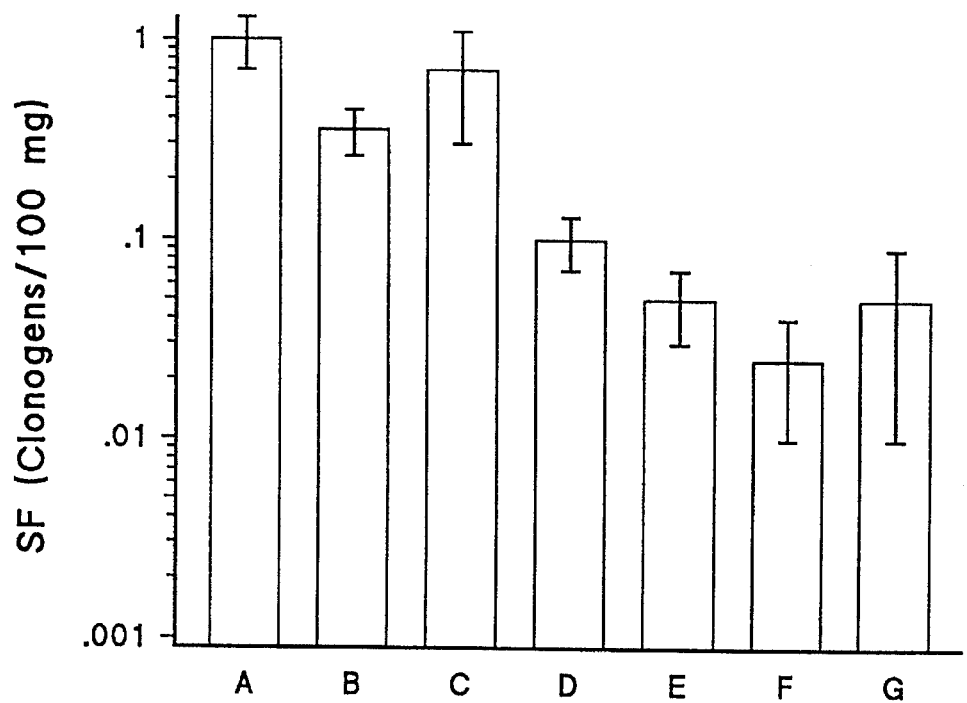
FIG. 4A shows the survival fraction (SF) of CaNT tumor cells following exposure of CBA/Gy fTO mice to (1) one of the compounds of this invention (CHL-HD), (2) hydralazine (HYDRAL), (3) control, (4) radiation (15 Gy), or (5) a combination of the compound (200 mg/kg) with radiation or HYDRAL (5 minutes before or 30 minutes after exposure to the compound).
Figure 4B:
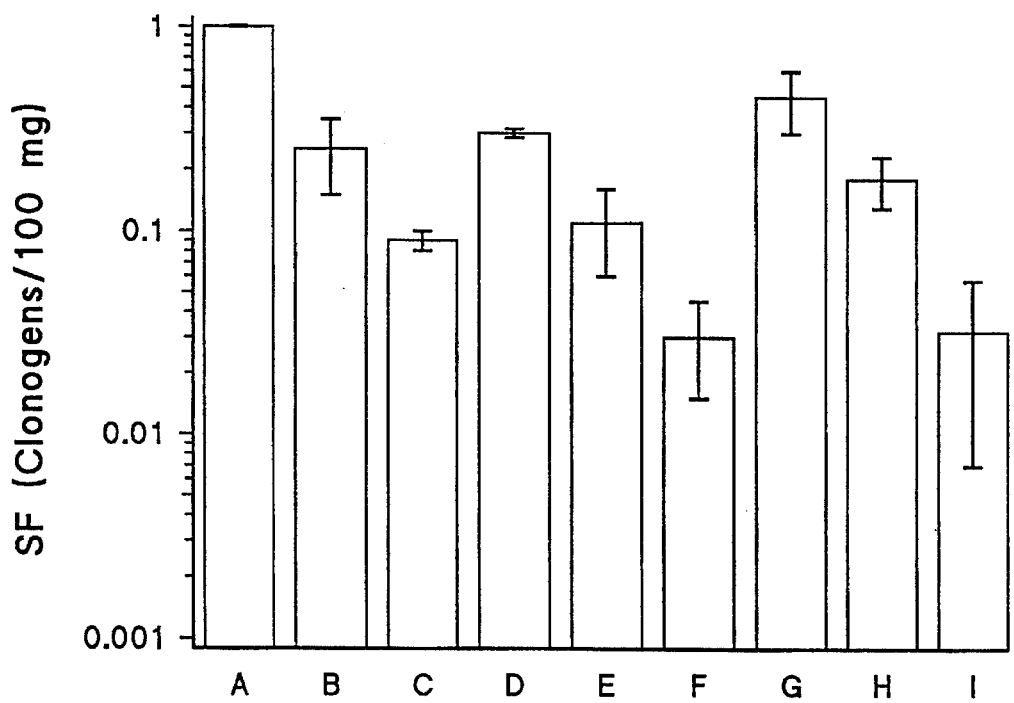
FIG. 4B shows the survival fraction (SF) of CaNT tumor cells following exposure of CBA/Gy/FTO mice to (1) chlorambucil (CHL), (2) hydralazine (HYDRAL), (3) a combination of CHL and HYDRAL, (4) CHLN-0, or (5) a combination of CHLN-O and HYDRAL.

FIG. 4A illustrates how the in vivo cytotoxicity of CHL-HD is potentiated by the administration of hydralazine 5 min prior or 30 post CHL-HD treatment. In addition, FIG. 4B illustrates that CHLN-O is less toxic than CHL, and its in vivo toxicity but not that of CHL can be potentiated by the administration of hydralazine.

EXAMPLE 8

Pharmaceutical Formulations

The invention also relates to pharmaceutical formulations containing such compounds. The formulation may also comprise one or more of such compounds together with one or more of (1) a pharmaceutically acceptable carrier, (2) a diluent, (3) an aqueous solution, (4) an adjuvant, or (5) another compound useful in treating hypoxic tumor cells. Suitable formulations may include buffered solutions containing one or more of the compounds administered as intravenous infusion.

The invention includes a method of medical treatment comprising the use of such compounds for hypoxic tumor cells. The method may also comprise using such compounds together with other methods of medical treatment useful in treating cancer, such as radiotherapy or chemotherapy.

While preferred embodiments have been described in detail, variations may be made to these embodiments without departing from the spirit or scope of the attached claims.

REFERENCES

Adams G E, Strafford I J. Biochem. Pharmacol. 35:71, 1986.
Adams G. E. Proc. Bioreductive Agents:Activation, Detoxification and Clinical Development Workshop Sept. 1992, Oxford UK.
Bremner J. C. M., Stratford I J, Bowler J and Adams G. E., Br. J. Cancer, 61 (1990) 717.
Brown J M. Br. J. Radiol 52:650–656, 1979.
Brown J M. J. Natl. Cancer Inst. 82:338–339, 1990.
Chandler K J, et al. J. Chromatog. B 652:195–202, 1993.
Chaplin D J, J Natl Can Inst. 81:618–622, 1989.
Chaplin D J, Olive P. L., Durand R. E. Cancer Res. 47:597–601, 1987.
Coleman C N, Doherty N., et al. Proc. Bioreductive Agents: Activation, Detoxification and Clinical Development Workshop September 1992, Oxford UK.
Coleman N J Nat. Canc. Inst. 80(5) 310–318, 1988.
Denny W A, Tercel M, Wilson W. R. International Conference on Bioreductive Drug Activation, August 1994, Lake Tahoe, Calif, U.S.A.
Disch, S. Anderson, P. J. Sealy, R. et al. Br. J. Radiol.56:251–255,1983.
Erlichman C. In: The Basic Sci. of Oncology (eds. Tannock and Hill) Pergamon Press 1987.
Fenton B M and Sutherland R. M., Int. J. Radiat. Oncol. Biol. Phys., 22:447, 1992.
Gatenby, R A. et al. Int. J. Radiat. Oncol. Biol. Phys. 14:831–838, 1988.
Grau C., Horsman M. and Overgaard J., Int. J. Radiat Oncol. Biol. Phys. 22: 415, 1992.
Hancock S. Int. Conf. Bioreductive Drug Activaiton Lake Tahoe, Calif. Aug. 16–19, 1994.
Hill R P. in I F Tannock and R P Hill (Editors), The Basic Science of Oncology, Pergamon Press, New York, 1987, p. 237. Ishidate M, Sakaroi Y, Matsui E. Chem Pharm Bull. 8:89–94, 1960.
Kennedy K A, Rockwell S, Sartorelli AC. Cancer Res. 40:2346–2360, 1980.
Kirkpatrick D L, Cancer Res. 47:4391–4395, 1987.
Kirkpatrick D L, et al. Anti-cancer Drugs 5: 467–472, 1994
Kirkpatrick L, Campbell K, Zhu L, Schroeder H. Proceedings of the 8th International Conference on Chemical Modifiers of Cancer Treatment, Jun. 16–19, 1993, Kyoto, Japan.
Kirkpatrick L, Schroeder H L, Chandler K, Anti-Cancer Drugs 5:467 –472, 1994.
Knox R J, Friedles F, et al. Bioc. Pharmacol. 37:4661–4669, 1988.
Mann J, Shervington L A J Cherm. Soc. Perkin. Trans 1:2961–2954, 1991.
Masters B. Williams C, Kamin H. Methods. Enzymol, 10:563,1967.
McLean A, Woods R L, Catovsky D., Farmer P., Cancer Treatment Reviews, 6:33–42, 1979.
Moulder, JE. Rockwell, S. Cancer Metastasis Rev. 5:313–341, 1987.
Olive P. L., Vikse C. and Trotter M J, Int. J. Radiation Oncology Biol. Phys., 22:397,1992.
Oosteen, E A Speckamp, W. N. Tetrahedron 43:255–262, 1987.
Owari S. Pharmaceutical Bull. 1:353–357, 1953.
Overgaard J. Int. Conf. Bioreductive Drug Activaiton Lake Tahoe, Calif. Aug. 16–19, 1994.
Papadopoulou M V, et al. Jpn. J. Can. Res. 83: 410–414, 1992.
Parkins C, Denekamp J, and Chaplin D J, Anticancer Res. 13:1437–1442, 1993.
Patterson L H Cancer Metast. Rev. 12:119–134, 1993.
Powis G. Hacker M. Toxicity of Anticancer Drugs Pergamon Press, Oxford, 1991.
Rice, G C et al. Proc. Natl. Acad. Sci. USA 83:9533–9537, 1988.
Rockwell S, Development of Target-Oriented Anti Cancer Drugs, Raven Press, New York, 1983, p. 157.
Sartorelli, AC. Cancer Res. 48:775–778, 1988.
Siemann D. Int. J. Radiation Oncology Biol. Phys., 22 (1992) 393.
Tannock I F and Hill R P (eds) The Basic Science of Oncology, Pergamon Press, New York 1987, p. 1.

Tannock I F, Rotin D. Cancer Res. 49:4373–4384, 1989.
Tannock, I. Guttman, P. Br. J. Cancer 43:245–248,1981.
Vaupel, P. et al. Cancer Res. 49:6449–6465,1989.
Verweij J. Int. Conf. Bioreductive Drug Activaiton Lake Tahoe, Calif. Aug. 16–19, 1994.
Walton et al., Int. J. Radiat. Oncol. Bio Phys. 16:983–986, 1989.
White I N H, Cahill A., Davies A., Carthew P. Arch. Toxicol. 66:100–106, 1992.
Wilson W R, Denny W. A. Proc. Bioreductive Agents: Activation, Detoxification and Clinical Development Workshop September. 1992, Oxford UK.
Workman P. and Stratford I J, Cancer Metast. Rev., 12:73–82, 1993.
Workman P. Cancer Topics 4:54–57, 1983.
Workman P., Int. Conf. Bioreductive Drug Activation, Lake Tahoe, 1994.
Workman P, Int. J. Radiation Oncology Biol. Phys., 22 (1992) 631.
Yasukochi Y. and Masters B. J. Biol. Chem. 251:5447–5344, 1976.
Zeman, E M et al. Int. J. Radiat. Oncol. Biol. Phys. 16:977–981,1989.

We claim:

1. A compound having the formula:

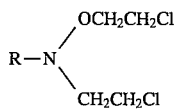

wherein R is selected from the group consisting of:

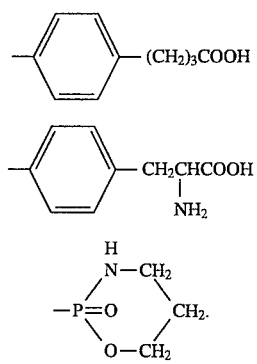

2. A compound as set out in claim 1 having the formula:

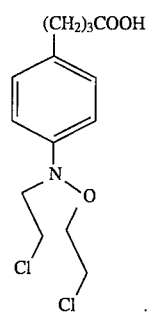

3. A compound as set out in claim 2 having the name 4-[p-(N-2-chloroethoxy N-2-chloroethylamino)phenyl] butanoic acid.

4. A salt of the compound set out in claim 2.

5. A salt as set out in claim 5 or claim 4 wherein the salt is HCl, tosylate or picrate.

6. A pharmaceutical formulation comprising a compound as set out in claim 2, or a salt of said compound, together with a pharmaceutically acceptable carrier or diluent.

7. A compound as set out in claim 2 together with another pharmaceutical.

8. A salt of a compound set out in claim 1.

9. A pharmaceutical formulation comprising a compound as set out in claim 1, or a salt of said compound, together with a pharmaceutically acceptable carrier or diluent.

10. A compound as set out in claim 1 together with another pharmaceutical.

11. A compound or salt thereof having the formula:

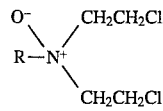

wherein R is selected from the group consisting of:

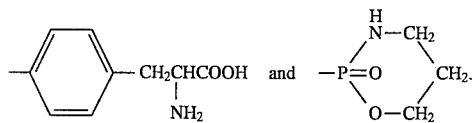

12. A pharmaceutical formulation comprising a compound as set out in claim 11, or a salt of said compound, together with a pharmaceutically acceptable carrier or diluent.

13. A pharmaceutical formulation comprising a compound as set out in claim 11 together with another pharmaceutical.

* * * * *